United States Patent

Olschimke

(10) Patent No.: US 8,863,479 B2
(45) Date of Patent: Oct. 21, 2014

(54) CONTAINER CONTAINING FLUORINATED ORGANIC CARBONATES

(75) Inventor: Jens Olschimke, Hannover (DE)

(73) Assignee: Solvay Fluor GmbH, Hannover (DE)

( * ) Notice: Subject to any disclaimer, the term of this patent is extended or adjusted under 35 U.S.C. 154(b) by 782 days.

(21) Appl. No.: 13/133,403

(22) PCT Filed: Dec. 14, 2009

(86) PCT No.: PCT/EP2009/067013
§ 371 (c)(1),
(2), (4) Date: Jun. 8, 2011

(87) PCT Pub. No.: WO2010/069893
PCT Pub. Date: Jun. 24, 2010

(65) Prior Publication Data
US 2011/0233104 A1    Sep. 29, 2011

(30) Foreign Application Priority Data
Dec. 15, 2008 (EP) .................................... 08171637

(51) Int. Cl.
*C07D 317/36* (2006.01)
*C07D 317/42* (2006.01)
*C07C 68/08* (2006.01)

(52) U.S. Cl.
CPC ............ *C07D 317/36* (2013.01); *C07D 317/42* (2013.01); *C07C 68/08* (2013.01)
USPC .............................................. 53/432; 53/510

(58) Field of Classification Search
CPC ......... B65B 31/00; B65B 31/04; B65D 81/00
USPC ................................................... 53/510, 432
See application file for complete search history.

(56) References Cited

U.S. PATENT DOCUMENTS

| | | | | |
|---|---|---|---|---|
| 4,528,799 | A * | 7/1985 | Olsen | 53/432 |
| 2004/0066749 | A1* | 4/2004 | Watanabe | 370/242 |
| 2006/0167279 | A1* | 7/2006 | Woo et al. | 549/229 |
| 2007/0287071 | A1* | 12/2007 | Chiga et al. | 429/332 |
| 2008/0160420 | A1* | 7/2008 | Adachi et al. | 429/332 |

FOREIGN PATENT DOCUMENTS

| | | | | |
|---|---|---|---|---|
| EP | 134687 | A * | 3/1985 |
| EP | 297372 | A2 * | 1/1989 |
| EP | 557167 | A1 * | 8/1993 |
| JP | 03200568 | A * | 9/1991 |

* cited by examiner

*Primary Examiner* — Thanh Truong
*Assistant Examiner* — Tara M Ho
(74) *Attorney, Agent, or Firm* — Beatrice C. Ortego

(57) ABSTRACT

A container containing a fluorinated organic carbonate and a gas atmosphere which contains a cover gas selected from the group consisting of a noble gas, e.g., argon, xenon, a gaseous fluorinated aliphatic carbon which is heavier than air and does not interfere with the fluorinated organic compound, $SF_6$, and any mixture thereof. Fluorinated organic carbonates are highly suitable as solvents or additives for solvent in Li ion batteries and consequently, must be kept in a very pure state even during expanded times of storage. The argon or xenon gas atmosphere prevents the intrusion of air or moisture even if the container is opened and the liquid handled in an environment of common air. A method of storing one or more fluorinated organic carbonates in a safe manner.

16 Claims, 2 Drawing Sheets

CONTAINER CONTAINING FLUORINATED ORGANIC CARBONATES

CROSS-REFERENCE TO RELATED APPLICATIONS

This application is a U.S. national stage entry under 35 U.S.C. §371 of International Application No. PCT/EP2009/067013 filed Dec. 14, 2009, which claims priority to European Patent Application No. 08171637.5 filed Dec. 15, 2008, this application being herein incorporated by reference in its entirety for all purposes.

The present invention concerns a container containing fluorinated organic carbonates and a method of storing fluorinated organic carbonates.

Fluorinated organic carbonates, especially fluorinated ethylene carbonates, fluorinated propylene carbonates and fluorinated dialkyl carbonates, for example, fluoromethyl methyl carbonate, are suitable as additives for Li ion batteries. High purity of these liquids is a necessary prerequisite for this purpose. The exclusion of water is very advantageous because of a possible hydrolytic reaction which may cause the formation of undesired side products.

The fluorinated organic carbonates are stored, after their manufacture, in containers for shipping and storage before use. Opening of these containers during filling them with the carbonates, transferring them or withdrawing them may cause the intrusion of air or moisture.

In the context of the present invention, the singular form is intended to include the plural, unless otherwise specified; and the plural is intended to include the singular unless otherwise specified. Thus, the term "carbonates" means that a single carbonate compound or a mixture of carbonate compounds can be concerned.

This problem is solved by the container of the present invention and the inventive method for storing fluorinated organic carbonates. The container of the present invention comprises container walls, an inner volume for storing of liquid goods, an opening for filling in goods to be stored or taking out the stored goods, a closure to close the opening to protect the stored goods against the environment, which container contains a fluorinated organic carbonate and a gas atmosphere which contains more than 50% by volume of a cover gas selected from the group consisting of a noble gas which is heavier than air, a gaseous fluorinated aliphatic carbon which is heavier than air and does not interfere with the fluorinated organic compound, and $SF_6$, and any mixture thereof. The opening can for example be a valve which is arranged the top of the container, for example, in a lid. Through the valve, liquid can be filled into the storage tank, or liquid can be taken our of the storage container. The term "to protect the stored goods against the environment" denotes especially a prevention of contact with air and moisture which often would be present around the container.

Figure 1:
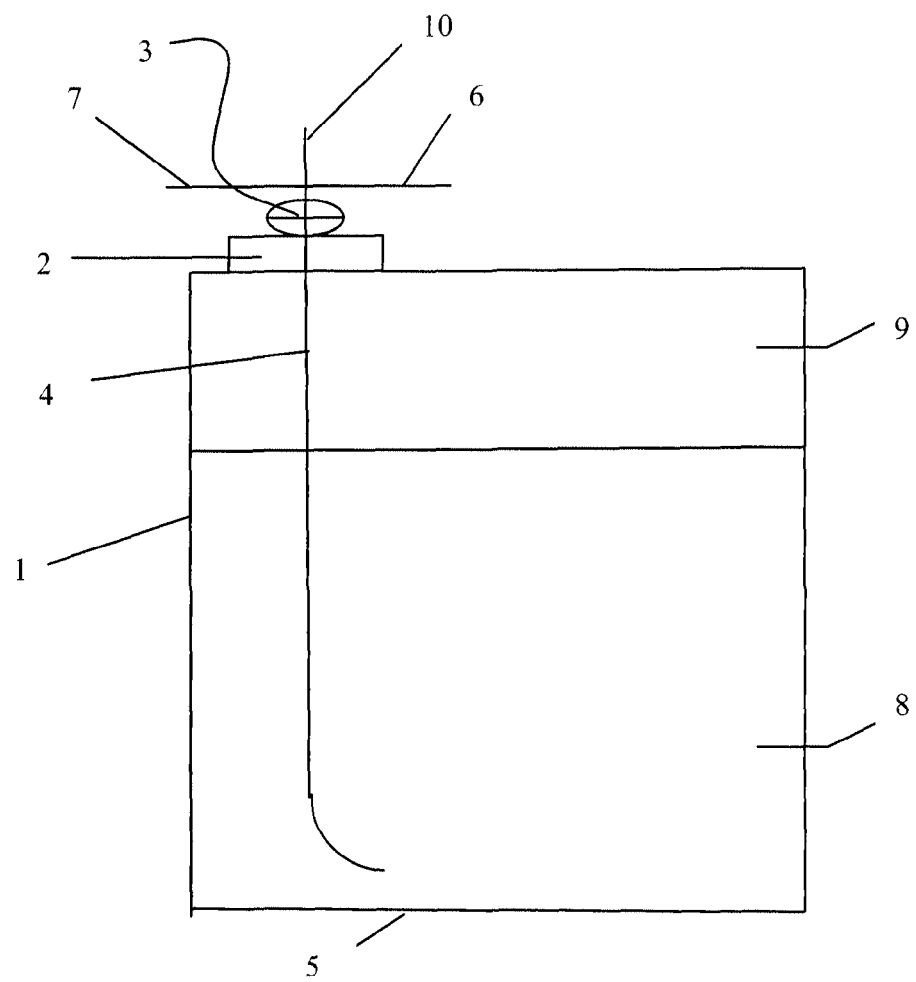
FIG. 1 shows a container of the invention. The container walls 1 are made from stainless steel. A valve 3 is screwed into lid 2 which is located in the upper wall of the container; valve 3 is connected to a hose 4 which extends close to the bottom 5 of the container. Valve 3 can be connected via line 6 to a source of noble gas (not enclosed in the figures), and via line 7 to a storage tank (also not enclosed in the figures) for fluorinated carbonates. The container contains fluorinated carbonate 8 which is covered by an argon atmosphere 9. Through line 10, any undesired over-pressurizing gas can be lead away from the container.
Figure 2:
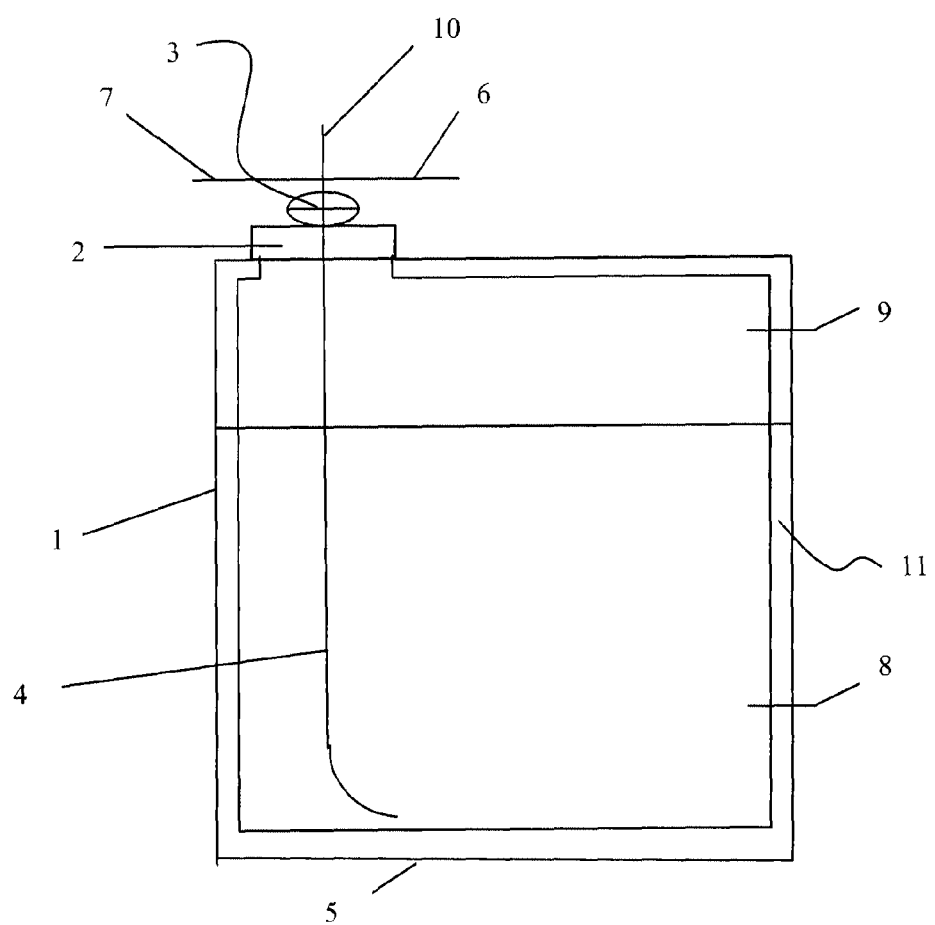
FIG. 2 shows a container which is made of common steel (not stainless steel). The walls 1 of the container are coated with a polyethylene lining 11. The other reference signs correspond to those of FIG. 1. A container as given in FIG. 2 can be used as one-way container because the steel walls are protected against direct contact with the liquid stored in the container.

The singular in the present invention is intended to include the plural. Also the term "noble gas" in the present invention includes the singular and the plural, thus, the atmosphere can contain single noble gas or a mixture of two or more noble gases. In the case that a single noble gas is contained, then ever-present trace amounts of other noble gases are neglected. For example, if the gas atmosphere contains 75% by volume of argon, the remainder to 100% by volume being nitrogen, then any possible trace amount of helium in the nitrogen or in the argon is neglected.

Preferably, the gas atmosphere contains equal to or more than 75 by volume of the cover gas, more preferably, equal to or more than 90% by volume, especially preferably, equal to or more than 99% by volume of the cover gas. Preferably, nitrogen, helium or any mixture thereof are the balance to 100% by volume, apart from possible undesired trace impurities like air or oxygen. Noble gases are preferred cover gases; argon and xenon are the preferred noble gas, especially argon.

The singular term "gaseous fluorinated aliphatic carbon" also includes the singular and plural. It denotes linear and branched aliphatic perfluorocarbons, i.e. compounds which consist of carbon and fluorine, and linear and branched aliphatic hydrofluorocarbons, i.e. compounds which consist of carbon, hydrogen and fluorine. The fluorocarbons must not react with the fluorinated organic carbonate and, considering the preferred use in Li ion batteries, preferably they must not react with other constituents of such batteries (e.g. with Li salts, non-fluorinated solvents, additives, electrode material etc). While it is possible to apply unsaturated perfluorocarbons and hydrofluorocarbons, it is preferred to apply saturated perfluorocarbons and hydrofluorocarbons. In general, said linear and branched aliphatic perfluorocarbons, i.e. the compounds which consist of carbon and fluorine, and linear and branched aliphatic hydrofluorocarbons, i.e. the compounds which consist of carbon, hydrogen and fluorine, especially the saturated perfluorocarbons and hydrofluorocarbons, do not interfere. The boiling point at standard pressure (1 bar abs.) is lower than 0° C., preferably lower than −10° C.

Compounds of formula (I), $C_xH_yF_z$ wherein x is an integer selected from 1 and 2, y is an integer selected from 0, 1 and 2, and z is (2x−y+2), having a boiling point at standard pressure of lower than 0° C. are very suitable as gas heavier than air. These compounds do not interfere with the fluorinated organic compound or with other constituents of Li ion batteries.

For example, $CH_2F_2$, $CHF_3$, $CF_4$, $C_2F_6$ and $C_3F_8$ are suitable fluorinated carbons.

Among the group of noble gases, $SF_6$, perfluorocarbons and hydrofluorocarbons, noble gases and $SF_6$ are preferred as cover gases; a noble gas is especially preferred as cover gas.

The invention will now be explained in further detail in view of the preferred embodiment, namely containers containing a fluorinated carbonate, one or more noble gases and an inert gas.

Preferably, the gas atmosphere in the container contains equal to or more than 75% by volume of the noble gas; argon and xenon and their mixtures are preferred noble gases. The reminder to 100% by volume is an inert gas which does neither interfere with the fluorinated organic carbonate nor with any other solvent or additive which might be later mixed with the fluorinated carbonate for the intended use as Li ion battery solvent. Preferably, the inert gas is selected from the group consisting of nitrogen, helium, sulfur hexafluoride and any mixture thereof. Nitrogen and helium are especially preferred as inert gases. Preferably, the gas atmosphere in the container contains equal to or more than 90% by volume of argon, xenon or mixtures thereof. More preferably, it contains equal to or more than 95% by volume of argon, xenon or mixtures thereof. Especially preferably, it contains equal to or more than 99% by volume of argon or xenon or mixtures thereof.

Argon is preferred. Essentially pure argon is especially preferred. "Essentially pure" denotes preferably argon with a purity of ≥99.0% by volume and more preferably, argon with a purity of ≥99.9% by volume.

The gas atmosphere could be kept under a pressure below 1 bar (abs.). Preferably, it is equal to or greater than 1 bar (abs.). The upper limit of the pressure in the gas atmosphere is dependent of the pressure admissible in respect safety concerns for the container, lines, valves, lids and other parts. Often, a pressure in the range of equal to or greater than 1 bar (abs.) and equal to or lower than 10 bar (abs.) is highly suitable.

The container can be made from any material compatible with fluorinated organic carbonates, for example, it can be made from stainless steel, fluorinated polymers, polyethylene or polypropylene. If desired, the container may be coated on the inside with materials compatible with fluorinated organic carbonates, e.g. with one of the polymers mentioned before. Containers, e.g. drums or bottles, made from aluminium or aluminium alloys, are also suitable.

The internal volume is not limited. Containers with a volume of equal to or greater than 10 ml internal volume are suitable for storing of fluorinated organic carbonates with a noble gas atmosphere. Containers with an internal volume of equal to or lower than 20.000 l or even more are suitable as well. Often, containers in the form of drums with an internal volume of about 30 l, 60 l, 200 l or 400 l are useful.

The containers are of a type the interior volume of which can be separated completely against the surrounding atmosphere to prevent intrusion of undesired substances. They have one or more means to fill in or withdraw liquid or gas, for example, valves or lids.

The containers contain, as mentioned above, fluorinated organic carbonates. Preferably, the fluorinated carbonates are selected from the group consisting of fluorinated dimethyl carbonate, fluorinated ethylene carbonate and fluorinated propylene carbonate. The fluorinated dimethyl carbonate and propylene carbonate may be substituted by one or more fluorine atoms, for example, they can be mono-fluorinated, difluorinated, trifluorinated, tetrafluorinated, pentafluorinated and hexafluorinated. The fluorinated ethylene carbonate can be monofluorinated, difluorinated, trifluorinated and tetrafluorinated. These compounds can be prepared, for example, by the reaction of the respective non-fluorinated organic carbonates with elemental fluorine, or from fluorinated organic carbonates with a lower degree of fluorination to obtain fluorinated organic carbonates with a higher degree of fluorination. Often, fluorination is performed with a neat starting material or with the starting material dissolved in a suitable solvent, for example, hydrogen fluoride or a perfluorocarbon. The elemental fluorine is often diluted by nitrogen; highly suitable mixtures contain 15 to 25% by volume of fluorine, the remainder being nitrogen. Fluorination is performed at lower temperatures for preparation of fluorinated organic carbonates with a lower degree of fluorination, e.g. in a range from −20° C. to 30° C. To obtain higher fluorinated organic carbonates, the reaction temperature may be slightly higher.

The higher fluorinated compounds may exist in isomers. These isomers are for example produced when, as described above, elemental fluorine is reacted with non-fluorinated organic carbonates or with fluorinated organic carbonates with a lower degree of fluorination, e.g. with the monofluorinated organic carbonates. Preferably, the container contains a fluorinated organic carbonate from the group consisting of fluoromethyl methyl carbonate, difluoromethyl methyl carbonate, bis-(fluoromethyl)carbonate, fluoroethylene carbonate (or 4-fluoro-1,3-dioxolane-2-one), 4,4-difluoro-1,3-dioxolane-2-one, 4,5-difluoro-1,3-dioxolane-2-one, 4,4,5-trifluoro-1,3-dioxolane-2-one, 4,4,5,5-tetrafluoro-1,3-dioxolane-2-one, fluoromethyl-ethylene carbonate (or 4-fluoromethyl-1,3-dioxolane-2-one), difluoromethyl ethylene carbonate (or 4-difluoromethyl-1,3-dioxolane-2-one), 4-methyl-4-fluoro-1,3-dioxolane-2-one, 4-methyl-5-fluoro-1,3-dioxolane-2-one, 4-fluoromethyl-4-fluoro-1,3-dioxolane-2-one, 4-fluoromethyl-5-fluoro-1,3-dioxolane-2-one, 4-methyl-4,4-difluoro-1,3-dioxolane-2-one and 4-methyl-4,5-difluoro-1,3-dioxolane-2-one. Of course, the container may contain two or more of fluorinated organic carbonates.

The fluorinated carbonates contained have preferably a degree of purity which makes them suitable to be used directly, without further distillation or recrystallization, as a solvent or as an additive for solvents in Li ion batteries. Preferably, the degree of purity is equal to or greater than 99.0% by weight, preferably equal to or greater than 99.9% by weight.

In one embodiment, the container is connected by respective lines with a gas storage tank for the cover gas, preferably it is connected with a storage tank for argon, xenon or their mixtures so that the respective gas can be supplied to the gas atmosphere of the container whenever liquid is withdrawn to prevent a vacuum to be formed. Generally, the cover gas, e.g., argon, xenon or mixture thereof will be pressurized in the gas storage tank, and thus, the gas in the gas storage tank can be applied to expel liquid out of the container. This makes withdrawal of the liquid very easy and at the same time prevents effectively any intrusion of undesired gases into the container.

In another embodiment, the container is not connected to a reservoir of gas atmosphere. But even if the container is opened in this case, the cover gas, preferably, argon or xenon or mixtures thereof effectively prevent air or moisture to enter the gas space in the container.

Another aspect of the present invention concerns a method of storing fluorinated organic carbonates. In this method, fluorinated organic carbonates are stored in a container comprising container walls, an inner volume for storing of liquid goods, an opening for filling in goods to be stored or taking out the stored goods, a closure to close the opening to protect the stored goods against the environment, which container contains the fluorinated carbonates and a gas atmosphere which contains equal to or more than 75% by volume of a cover gas selected from the group consisting of noble gas which is heavier than air, a gaseous fluorinated aliphatic carbon which is heavier than air and does not interfere with the fluorinated organic compound, and $SF_6$, or any mixture thereof. The cover gas is preferably selected from argon, xenon and mixtures thereof. The reminder to 100% by volume is an inert gas, preferably, helium, nitrogen or any mixture thereof. Preferably, the atmosphere in the container contains equal to or more than 90% by volume of argon or xenon.

More preferably, it contains equal to or more than 95% by volume of argon or xenon. Especially preferably, it contains equal to or more than 99% by volume of argon or xenon. Mixtures of argon and xenon are also applicable.

Argon is preferred. Essentially pure argon is especially preferred. "Essentially pure" denotes preferably argon with a purity of 99.9% by volume.

Preferably, the method of the invention includes a step of filling the container with the fluorinated organic carbonate. Optionally, the container may be purified, for example, by applying a vacuum to remove any contained water, air or other impurities in the container. Optionally, some pure fluorinated organic carbonate of the type which shall be stored later in the container can be used as purifying liquid to clean the internal volume of the container, valves, or lines. The cover gas, preferably argon, xenon or their mixtures, and especially preferably argon, is filled into the container to substitute 50% by volume or more, preferably 75% by volume or more of any gas actually present in the gas atmosphere of the container. Preferably, the gas atmosphere present in the container is completely flushed. Finally, the fluorinated organic carbonate is supplied into the container whereby a part of the gas atmosphere is replaced or withdrawn from the container.

Preferably, the method according to the invention also includes a step of removing liquid from the container. In this step, liquid is removed, e.g. by a pump, and, preferably, the pressure of the gas atmosphere is kept essentially constant. For example, as explained above, a gas storage tank can be connected to the container, and when liquid is removed from the container, gas from the gas storage tank is supplied to the container. The gas atmosphere in the gas storage tank—preferably it has the same constitution as the gas atmosphere actually in the container—may be applied to pressurize the storage container. This prevents any external gas to enter the internal volume of the container, and it may make withdrawal of liquid from the container easier; the liquid must not be pumped out, but it is sufficient to open, for example, a valve.

Optionally, the gas atmosphere in the container can be substituted from time to time to safeguard that no gaseous impurities or moisture enter the container.

Accordingly, the method of the invention further comprises at least one step from the group consisting of:
a) flushing the container with a gas atmosphere containing more than 50% by volume of a cover gas selected from the group consisting of noble gas heavier than air before filling the fluorinated carbonate into the container;
b) supplying a gas atmosphere containing more than 50% by volume of a cover gas selected from the group consisting of a noble gas heavier than air, a gaseous fluorinated aliphatic carbon which is heavier than air and does not interfere with the fluorinated organic compound, and $SF_6$, and any mixture thereof, to the container to compensate for the amount of fluorinated organic carbonate withdrawn from the container;
c) flushing the gas atmosphere with fresh a gas atmosphere containing more than 50% by volume of a cover gas selected from the group consisting of a noble gas heavier than air, a gaseous fluorinated aliphatic carbon which is heavier than air and does not interfere with the fluorinated organic compound, and $SF_6$, and any mixture thereof; and
d) pressurizing the container with a gas atmosphere containing more than 50% by volume of a cover gas selected from the group consisting of a noble gas heavier than air, a gaseous fluorinated aliphatic carbon which is heavier than air and does not interfere with the fluorinated organic compound, and $SF_6$, and any mixture thereof.

Also in this embodiment, the cover gas is preferably selected from argon, xenon and mixtures thereof. Especially preferably, the cover gas is argon.

The preferred embodiments of the noble gas containing atmosphere correspond to those mentioned above (i.e. preferably, equal to or more than 75% by volume of a noble gas is contained in the gas atmosphere, the noble gas preferably is selected from the group consisting of argon, xenon and their mixtures, argon is especially preferred etc). Here, the gas atmosphere used for flushing must not necessarily be identical with the gas atmosphere used for pressurizing or the supply to compensate for withdrawn liquid.

The container and the method of the invention provides for a storing of fluorinated organic carbonates wherein contamination of the stored carbonate can effectively be prevented. The argon or xenon gas atmosphere prevents the intrusion of air or moisture even if the container is opened and the liquid handled in an environment of common air.

The following example explains the invention in further detail without intention to limit it.

EXAMPLE 1

Container Containing Fluoroethylene Carbonate 1.1. Preparation fluoroethylene carbonate, F1EC (4-fluoro-1,3-dioxolane-2-one)

Fluoroethylene carbonate ("F1EC") is produced according to the method described in US-2006-0036102. A solution of ethylene carbonate in fluoroethylene carbonate was reacted with elemental fluorine, diluted with nitrogen (volume ratio of $F_2:N_2=1:4$). The resulting reaction product is isolated as described in US-2006-0036102. Fluoroethylene carbonate with a purity of >99.9% by weight (determined by gas chromatography) is obtained.

1.2. Storing of F1EC

A 30 l container made from stainless steel is flushed with argon having a purity greater than 99.9% by volume. Then, highly pure fluoroethylene carbonate is used as purifying liquid to contact internal surfaces of the container to remove any adhering moisture, dust or other contaminants. After removal of the resulting liquid, a valve is screwed into a respective opening of the container in the lid. The valve allows complete closing of the container. It can be connected to a line in connection with a storage tank for protective gas atmosphere. Via this line, the container is again flushed with highly pure argon. The gas leaves the container via another opening in the valve and an off-gas line through the valve. Then, the desired amount of fluoroethylene carbonate is filled into the container through the other tap of the valve which further is connected to a hose reaching down to the bottom of the container. The valve of the container is then closed; alternatively, the valve is removed, and the lid is closed, e.g. by a fitting screw. In this manner, the liquid can be stored until all or only a part of it is removed from the container through a hose which extends into the liquid and which is connected via the valve to another storage tank. During removal of liquid, argon is supplied into the container, thus preventing any air or moisture from entering the internal space of the container.

1.3. Storing of F1EC Under $SF_6$

The container of example 1.2. is used, filled with F1EC. This time, $SF_6$ with a purity of 99% by volume, the remainder to 100% by volume being nitrogen, is used as protective gas atmosphere.

1.4. Storing of Fluoromethyl Methyl Carbonate (F1DMC)

In the container of example 1.2., F1DMC is filled. A mixture containing 75% by volume of argon, the remainder to 100% volume being nitrogen, is used as protective atmosphere.

1.5. Storing of F1EC Under $CF_4/N_2$

The container of example 1.2. is used, filled with F1EC. This time, a gas atmosphere containing 95% by volume $CF_4$ and 5% by volume of $N_2$ is used for protection against intrusion of air and moisture.

1.6. Storing of F1EC Under $Ar/N_2$

The container of example 1.2. is used, filled with F1EC. This time, a gas atmosphere containing 75% by volume of argon, purity>99% by volume, and 25% by volume of $N_2$ is used for protection against intrusion of air and moisture.

1.7. Storing of F2EC Under Ar

The container of example 1.2. is used, filled with 4,5-difluoro-1,3-dioxolane-2-one (F2EC). This compound is prepared in the same manner as F1EC, but with a higher ratio of $F_2$:EC. This time, a gas atmosphere containing 75% by volume of argon, purity>99% by volume, and 25% by volume of $N_2$ is used for protection against intrusion of air and moisture.

1.8. Storing of F1EC Under $Ar/N_2$

The container of example 1.2. is used, filled with F1EC. This time, a gas atmosphere containing 75% by volume of argon, purity>99% by volume, and 25% by volume of $N_2$ is used for protection against intrusion of air and moisture.

1.9. Safe Withdrawal of F1EC from the Storage Container

A storage container as described in example 1.1 is used. The connection of the valve to the argon line is opened, and then, through the hose, the valve and a line to a storage tank, liquid is pumped out of the container. Afterwards, both connections are closed. No air or moisture can enter the container.

2. Storing of F1EC in a Steel Container

Example 1.2 is repeated, but this time, a 30 l container made from common steel is used. The inside of the container walls are coated with a polyethylene lining. Due to the cheap material, this container can be handled as one-way container.

The invention claimed is:

1. A container containing container walls, an inner volume for storing of liquid goods, an opening for filling in goods to be stored or taking out the stored goods, a closure to close the opening to protect the stored goods against the environment, said container containing a fluorinated organic carbonate and a gas atmosphere, said gas atmosphere containing more than 50% by volume of a cover gas selected from the group consisting of a noble gas which is heavier than air, a gaseous fluorinated aliphatic carbon which is heavier than air and does not interfere with the fluorinated organic carbonate, $SF_6$, and a mixture thereof.

2. The container according to claim 1, wherein the gas atmosphere contains equal to or more than 75% by volume of a noble gas.

3. The container according to claim 1, wherein the noble gas is selected from the group consisting of argon, xenon, and mixtures thereof.

4. The container according to claim 3, a wherein the gas atmosphere consists essentially of pure argon.

5. The container according to claim 1, being manufactured from stainless steel, polyethylene, polypropylene, aluminum, or aluminum alloys.

6. The container according to claim 1, wherein the fluorinated organic carbonate is selected from the group consisting of fluorinated dimethyl carbonate, fluorinated ethylene carbonate, fluorinated propylene carbonate, and mixtures of two or more thereof.

7. The container according to claim 1, wherein the fluorinated organic carbonate is selected from the group consisting of fluoromethyl methyl carbonate, difluoromethyl methyl carbonate, bis-(fluoromethyl) carbonate, fluoroethylene carbonate (or 4-fluoro-1,3-dioxolane-2-one), 4,4-difluoro-1,3-dioxolane-2-one, 4,5-difluoro-1,3-dioxolane-2-one, 4,4,5-trifluoro-1,3-dioxolane-2-one, 4,4,5,5-tetrafluoro-1,3-dioxolane-2-one, fluoromethyl-ethylene carbonate (or 4-fluoromethyl-1,3-dioxolane-2-one), difluoromethyl ethylene carbonate (or 4-difluoromethyl-1,3-dioxolane-2-one), 4-methyl-4-fluoro-1,3-dioxolane-2-one, 4-methyl-5-fluoro-1,3-dioxolane-2-one, 4-fluoromethyl-4-fluoro-1,3-dioxolane-2-one, 4-fluoromethyl-5-fluoro-1,3-dioxolane-2-one, 4-methyl-4,4-difluoro-1,3-dioxolane-2-one, 4-methyl-4,5-difluoro-1,3-dioxolane-2-one, and mixtures of two or more thereof.

8. The container according to claim 1, wherein the fluorinated organic carbonate is equal to or more than 99.9% by weight pure.

9. A method of storing one or more fluorinated organic carbonates, comprising storing a fluorinated organic carbonate in a container comprising container walls, an inner volume for storing of liquid goods, an opening for filling in liquid goods to be stored or taking out the stored goods, and a closure to close the opening to protect the stored liquid goods against the environment, wherein said container contains said fluorinated organic carbonate and a gas atmosphere which contains more than 50% by volume of a cover gas selected from the group consisting of a noble gas which is heavier than air, a gaseous fluorinated aliphatic carbon which is heavier than air and does not interfere with the fluorinated organic carbonate, $SF_6$, and any mixture thereof.

10. The method according to claim 9, wherein the noble gas is selected from the group consisting of argon, xenon, and mixtures thereof.

11. The method according to claim 10, wherein the gas atmosphere contains equal to or more than 95% by volume of argon or xenon.

12. The method according to claim 11, wherein the gas atmosphere contains equal to or more than 99% by volume of argon or xenon.

13. The method according to claim 12, wherein the gas atmosphere consists essentially of pure argon.

14. The method of claim 9, further comprising at least one step from the group consisting of:
  a) flushing the container with a gas atmosphere containing more than 50% by volume of a cover gas selected from the group consisting of a noble gas heavier than air, a gaseous fluorinated aliphatic carbon which is heavier than air and does not interfere with the fluorinated organic carbonate, $SF_6$, and any mixture thereof, before filling the fluorinated organic carbonate into the container;
  b) supplying a gas atmosphere containing more than 50% by volume of a cover gas selected from the group consisting of a noble gas heavier than air, a gaseous fluorinated aliphatic carbon which is heavier than air and does not interfere with the fluorinated organic carbonate, $SF_6$, and any mixture thereof, to the container to compensate for an amount of the fluorinated organic carbonate which is withdrawn from the container;
  c) flushing the gas atmosphere present in the container with a fresh gas atmosphere containing more than 50% by volume of a cover gas selected from the group consisting of a noble gas heavier than air, a gaseous fluorinated aliphatic carbon which is heavier than air and does not interfere with the fluorinated organic carbonate, $SF_6$, and any mixture thereof; and d) pressurizing the container with a gas atmosphere containing more than 50% by volume of a cover gas selected from the group consisting of a noble gas heavier than air, a gaseous fluorinated aliphatic carbon which is heavier than air and does not interfere with the fluorinated organic carbonate, $SF_6$, and any mixture thereof.

15. The method of claim 14, wherein the cover gas is selected from the group consisting of argon, xenon, and mixtures thereof.

16. The method of claim 9, wherein the gas atmosphere contains equal to or more than 75% by volume of the noble gas.

* * * * *